United States Patent [19]
Wainer et al.

[11] Patent Number: 5,830,672
[45] Date of Patent: Nov. 3, 1998

[54] ELISA KIT FOR THE RAPID DETERMINATION OF N-ACETYLTRANSFERASE (NAT2) PHENOTYPES

[76] Inventors: Irving W. Wainer, 4028 Dorchester, Westmount, Québec, Canada, H3Z 1T8; Pierre Wong, 3415 Aylmer, Apt. 4, Montréal, Quebec, Canada, H2X 2B4; Brian Leyland-Jones, 1455 Sherbrooke, #412, Montréal, Québec, Canada, H3G 1L2

[21] Appl. No.: 594,934

[22] Filed: Jan. 31, 1996

[51] Int. Cl.$^6$ .................. G01N 33/53; G01N 33/574; G01N 33/573
[52] U.S. Cl. .................. 435/7.9; 435/7.23; 435/7.92; 435/7.93; 435/15; 435/7.4; 436/64; 436/813
[58] Field of Search .................. 435/7.23, 7.9, 435/7.92, 7.93, 15, 7.4; 436/64, 813

[56] References Cited

FOREIGN PATENT DOCUMENTS 9504757  2/1995  WIPO .

OTHER PUBLICATIONS

Carr, A. et al. (1994) *AIDS*, 8:333–337.
Fickling, S.A. et al. (1990) J. Immunol. Meth., 129:159–164.
Fink, K. et al. (1964) J. Biol. Chem., 239:4250–4256.
Kalow, W. et al. (1993) Clin. Pharmacol. Ther., 53:503–514.
Kilbane, A.J. et al. (1990) Clin. Pharmacol. Ther., 47:470–477.
Lloyd, D. et al. (1992) J. Chrom., 578:283–291.
Lowry, O.H. et al. (1951) J. Biol. Chem., 193:265–275.
Meyer, U.A. (1994) Proc. Natl. Acad. Sci. USA, 91:1983–1984.
Ratain, M. J. et al. (1993) Cancer Research, 53:2304–2308.
Tang, B–K. et al. (1991) Clin. Pharmacol. Ther., 49:648–657.
Wong, P., Leyland–Jones, B., and Wainer, I.W. (1995) J. Pharm. Biomed. Anal., 13:1079–1086.

*Primary Examiner*—Toni R. Scheiner
*Attorney, Agent, or Firm*—Swabey Ogilvy Renault; France Côté ; Paul Marcoux

[57] ABSTRACT

The invention relates to an enzyme linked immunosorbent assay (ELISA) kit for the rapid determination of N-acetyltransferase (NAT2) phenotype which can be used on a routine basis in a clinical laboratory. The ELISA kit allows physicians to: a) individualize therapy of drugs such as amrinone, procainamide, amonafide, dapsone, isoniazid, trimethoprim-sulphamethoxazole (TMP-SMX) and b) to predict susceptibility to carcinogen induced diseases such as bladder and colon rectal cancers.

16 Claims, 7 Drawing Sheets

AAMU-hemisuccinic acid    1 methyl xanthine-8-propionic acid

Derivatives of AAMU (5-acetamino-6-amino-3-methyluracil) or
AFMU (5-acetamino-6-formylamino-3-methyluracil)

Where Y is

H or     C—H
         ||
         O

X (CH$_2$)n—COOH          where n = 2, 3 or 4

CH$_2$—X'              where X' is I, Br, or Cl

CH$_2$—S—(CH$_2$)n—NH$_2$

CH$_2$—S—CH$_2$—CH$_2$—OH

Derivatives of AAMU (5-acetamino-6-amino-3-methyluracil) or
AFMU (5-acetamino-6-formylamino-3-methyluracil)

Where Y is

H or $\underset{O}{\overset{}{C}}-H$ (C=O, H)

X (CH$_2$)n—COOH                         where n = 2, 3 or 4

CH$_2$—X'                                where X' is I, Br, or Cl

CH$_2$—S—(CH$_2$)n—NH$_2$

CH$_2$—S—CH$_2$—CH$_2$—OH

Derivatives of 1X (methylxanthine)

X where n = 2, 3 or 4

(CH$_2$)n—C—NH—(CH$_2$)n—SH
         ‖
         O

Derivatives of 1X (methylxanthine)

X where n = 2, 3 or 4

$(CH_2)n-\underset{\underset{O}{\|}}{C}-NH-(CH_2)n-SH$

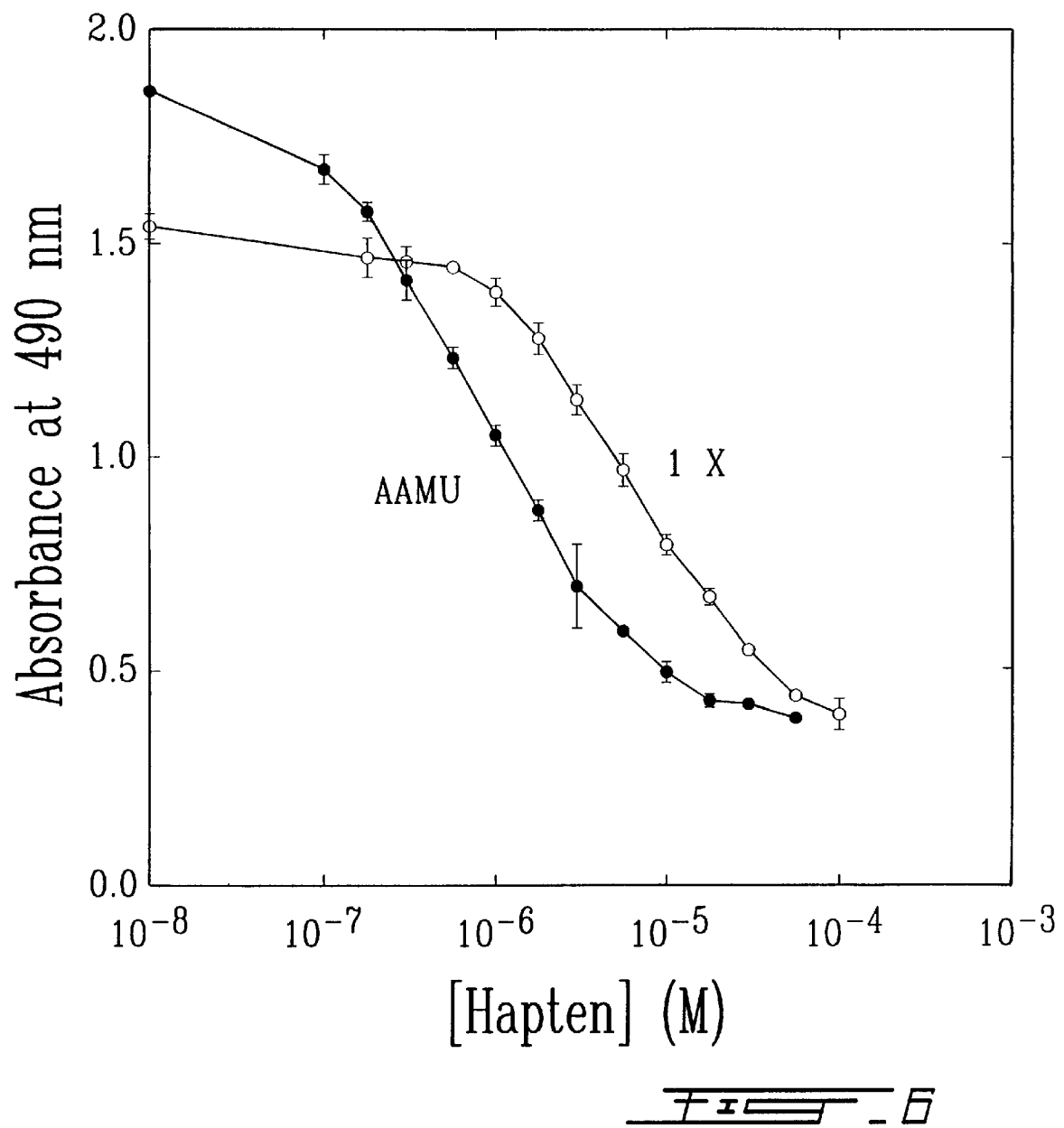
FIG_6

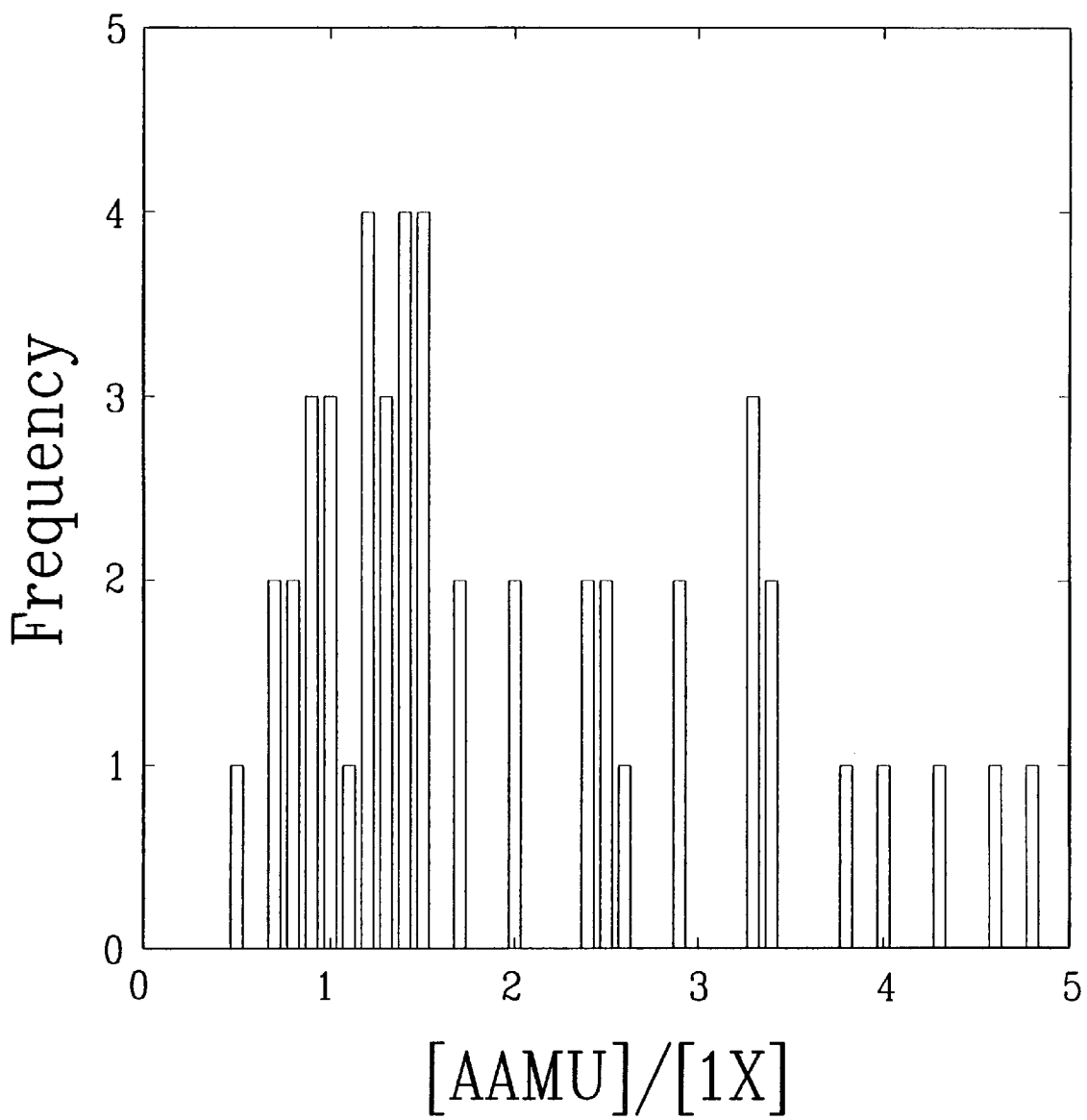
FIG_7

ELISA KIT FOR THE RAPID DETERMINATION OF N-ACETYLTRANSFERASE (NAT2) PHENOTYPES

BACKGROUND OF THE INVENTION (a) Field of the Invention

The invention relates to an enzyme linked immunosorbent assay (ELISA) kit for the rapid determination of N-acetyltransferase (NAT2) phenotype which can be used on a routine basis in a clinical laboratory, and which allows a physician to: a) individualize therapy of drugs such as amrinone, procainamide, amonafide, dapsone, isoniazid, trimethoprim-sulphamethoxazole (TMP-SMX) and b) to predict susceptibility to carcinogen induced diseases such as bladder and colonrectal cancers.

(b) Description of Prior Art

The fate of drugs (or xenobiotics) administered to humans is generally their metabolism in the liver into a form less toxic and lipophilic with their subsequent excretion in the urine. Their metabolism involves two systems which act generally consecutively: the cytochrome P450 system which includes at least 20 enzymes catalyzing oxidation reactions and localized in the microsomal fraction, and the conjugation system which involves a set of at least five enzymes. An enzyme of one system can act on several drugs and drug metabolites. The rate of metabolism of a drug may differ between individuals and between ethnic groups, owing to the existence of enzymatic polymorphism within each system. Two phenotypes can be distinguished: poor metabolizers (PM) and extensive metabolizers (EM). Knowledge of the phenotype is useful clinically because: a) the phenotype is associated with toxicities in chemical plants, diseases and cancers; b) it allows to prescribe a drug regimen on the individual basis; c) it provide a rationale in the design of therapeutic drugs. Currently, the phenotype is determined by measurements of the ratio of two metabolites of the drug or a probe drug in urine samples by high pressure liquid chromatography (HPLC) or capillary electrophoresis (CE), hence using methods which are not readily available in a clinical laboratory.

N-Acetylation Polymorphism

Individuals are genetically polymorphic in their rate of N-acetylation of drugs via the N-acetyltransferase (NAT2) pathway (Meyer, U. A. (1994) *Proc. Natl. Acad. Sci. USA*, 91:1983–1984). Two major metabolic phenotypes can be distinguished: fast and slow N-acetylators. Drugs that are subject to N-acetylation polymorphism include sulfonamides (sulfamethazine), antidepressants (phenelzine), antiarrhymics (procainamide), and antihypertensives (hydrazine). Some adverse therapeutic consequences of the acetylator phenotype are peripheral neurophathy and hepatitis. In an opposite manner, the N-acetylation of procainamide produces a therapeutically active metabolite with reduced toxicity. N-acetylation polymorphism has also been linked to detoxification pathway of some environmental carcinogenic arylamines and there is a higher frequency of bladder cancers among chemical dye workers who are slow N-acetylators.

Inter ethnic Differences

The frequency of PM and EM (autosomal recessive trait) show considerable inter ethnic differences for the N-acetylation polymorphism. In Caucasians, the frequencies are approximately 60 and 40%, while in Orientals, they are 20 and 80% (Meyer, U. A. (1994) *Proc. Natl. Acad. Sci. USA*, 91:1983–1984). It is reasonable that, in drug metabolism studies, each ethnic group be studied separately for evidence of polymorphism and its antimode should not be extrapolated from one ethnic population to another Amonafide A recent sample of the importance of phenotyping in drug management for chemotherapy is amonafide (Ratain, M. J. et al. (1993) *Cancer Research*, 53:2804–2808). Amonafide is a new site-specific intercalating, antineoplastic agent which is converted to an active metabolite by way the N-acetyltransferase (NAT2) pathway. Studies have shown a direct correlation between toxicity and the acetylator phenotype, with rapid acetylators at greater risk to problems of severe toxicity. However, some cytotoxicity is necessary for therapeutic benefit. Therefore, knowing the patient's acetylator phenotype can aid the physician in designing a drug regimen which balances efficacy and toxicity.

HIV-infected patients

Slow acetylators have an increased risk of cutaneous hypersensitivity to multiple drugs that are metabolized by acetylation, including sulfonamides and dapsone (Carr, A. et al. (1994) *AIDS*, 8:333–337). Hypersensitivity to trimethoprim-sulphamethoxazole (TMP-SMX) is more common in patients with HIV infection. It has been demonstrated that patients with HIV disease have an increased prevalence of the slow acetylator phenotype (90%). Thus, knowledge of their acetylator phenotype in the use of this particular drug.

Individualized Therapy

As is well known that it is possible to individualize therapy for a large number of drugs (theophylline, digoxin, aminoglycosidases, etc.). However, individualization of therapy has been extremely slow to develop because the methods used for drug phenotyping involves high pressure liquid chromatography (HPLC) and capillary electrophoresis (CE), which are costly, time consuming, and require expertise not readily applicable in a clinical laboratory.

It would be highly desirable to be provided with a method for determining an individual's N-acetylation phenotyping using non-toxic drug so as to predict his/her response and side effect profile to a wide range of potentially toxic drugs.

It would be highly desirable to be provided with an enzyme linked immunosorbent assay (ELISA) kit for N-acetyltransferase (NAT2) phenotyping which could be accomplished on routine basis by any technicians with a minimum of training and does not involve complex equipments.

It would be highly desirable to be provided with an ELISA kit which would enable a physician to individualize therapy of drugs such as amrinone, procainamide, amonafide, dapsone, isoniazid, trimethoprim-sulphamethoxazole (TMP-SMX).

SUMMARY OF THE INVENTION

One aim of the present invention is to provide a method for determining an individual's N-acetylation phenotyping using a non-toxic drug so as to predict his/her response and side effect profile to a wide range of potentially toxic drugs.

Another aim of the present invention is to provide an enzyme linked immunosorbent assay (ELISA) kit for the rapid determination of N-acetyltransferase (NAT2) phenotype which can be used on a routine basis in a clinical laboratory.

Another aim of the present invention is to provide an ELISA kit which allows a physician to: a) individualize therapy of drugs such as amrinone, procainamide, amonafide, dapsone, isoniazid, trimethoprim-sulphamethoxazole (TMP-SMX) and b) to predict susceptibility to carcinogen induced diseases such as bladder and colonrectal cancers.

BRIEF DESCRIPTION OF THE DRAWINGS

FIG. 6 illustrates the absorbance competitive antigen ELISA curves of AAMU-Ab and 1X-Ab in accordance with one embodiment of the present invention; and FIG. 7 is an histogram of molar ratio of AAMU/1X.

DETAILED DESCRIPTION OF THE INVENTION

Figure 1:
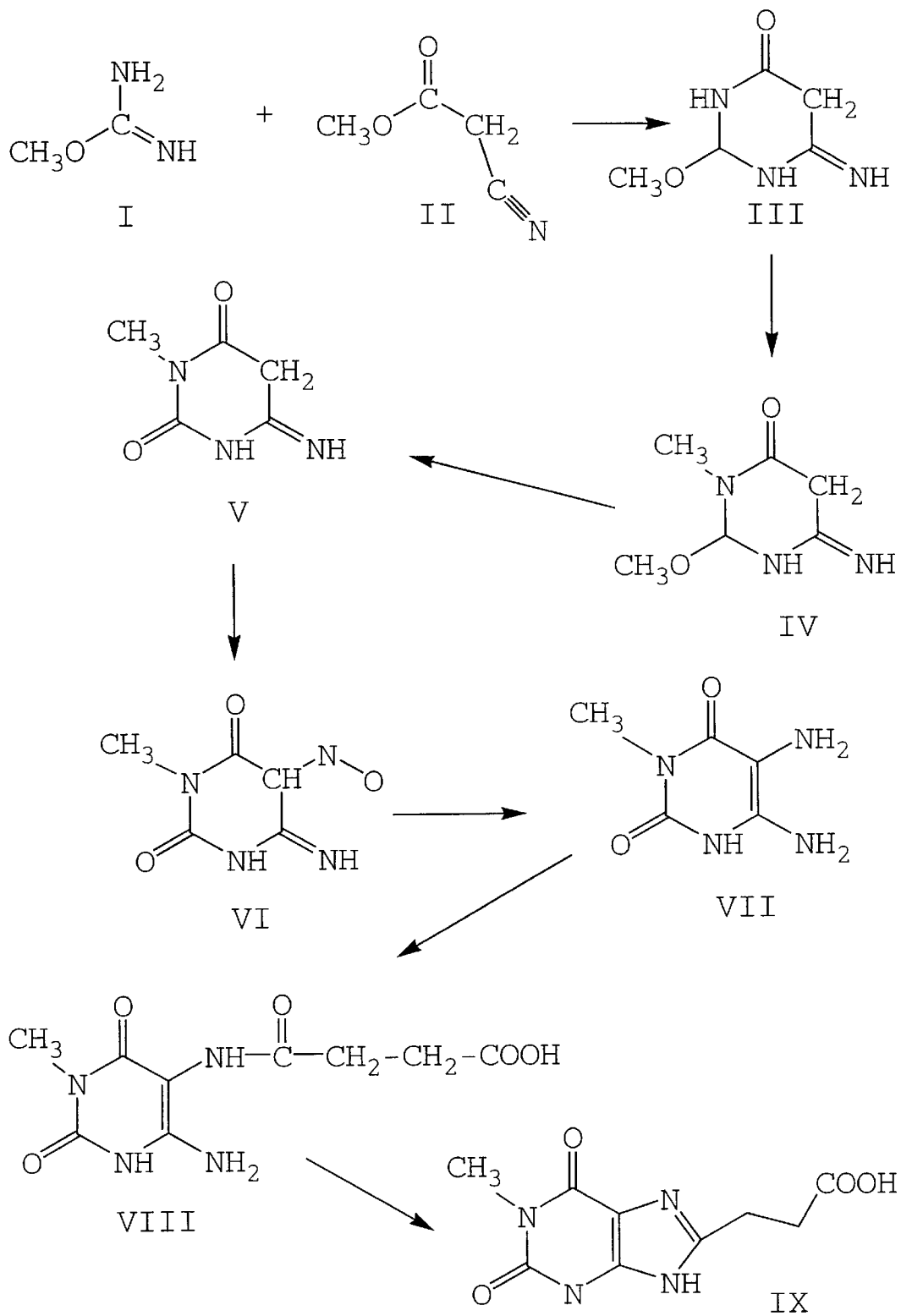
FIG. 1 illustrates the synthetic routes for the production of AAMU and 1X derivatives used in accordance with one embodiment of the present invention.

Different probe drugs can be used to determine the NAT2 phenotype (Kilbane, A. J. et al. (1990) *Clin. Pharmacol. Ther.*, 47:470–477; Tang, B-K. et al. (1991) *Clin. Pharmacol. Ther.*, 49:648–657). In accordance with the present invention caffeine is the preferred probe because it is widely consumed and relatively safe (Kalow, W. et al. (1993) *Clin. Pharmacol. Ther.*, 53:503–514). In studies involving this probe, the phenotype has been generally determined from ratios of the caffeine metabolites 5-acetamino-6-amino-1-methyluracil (AAMU) or 5-acetamino-6-formylamino-1-methyluracil (AFMU) and 1-methylxanthine (1X). In these studies, the subjects are given an oral dose of a caffeine-containing substance, and the urinary concentrations of the target metabolites determined by HPLC (Kilbane, A. J. et al. (1990) *Clin. Pharmacol. Ther.*, 47:470–477; Tang, B-K. et al. (1991) *Clin. Pharmacol. Ther.*, 49:648–657) or CE (Lloyd, D. et al. (1992) *J. Chrom.*, 578:283–291).

The number of clinical protocols requiring the determination of NAT2 phenotypes is rapidly increasing and in accordance with the present invention, an enzyme linked immunosorbent assay (ELISA) was developed for use in these studies (Wong, P., Leyland-Jones, B., and Wainer, I. W. (1995) *J. Pharm. Biomed. Anal.*, 13:1079–1086). ELISAs have been successfully applied in the determination of low amounts of drugs and other antigenic components in plasma and urine samples, involve no extraction steps and are simple to carry out.

In accordance with the present invention, antibodies were raised in animals against two caffeine metabolites [5-acetamino-6-amino-1-methyluracil (AAMU) or 5-acetamino-6-formylamino-1-methyluracil (AFMU) and 1-methyl xanthine (1X)] present in urine samples of an individual collected after drinking coffee. Their ratio provides a determination of an individual's N-acetylation (NAT2) phenotype. Subsequently, there was developed a competitive antigen enzyme linked immunosorbent assay (ELISA) for measuring this ratio using these antibodies.

The antibodies of the present invention can be either polyclonal antibodies or monoclonal antibodies raised against two different metabolites of caffeine, which allow the measurement of the molar ratio of these metabolites.

In accordance with the present invention, the molar ratio of caffeine metabolites is used to determine the acetylation phenotype of the individual as follows. Individuals with a ratio less than 1.80 are slow acetylators.

Materials and Methods

Materials

Cyanomethylester, isobutyl chloroformate, dimethylsulfate, sodium methoxide, 95% pure, and tributylamine were purchased from Aldrich (Milwaukee, Wis., USA); horse radish peroxidase was purchased from Boehringer Mannheim (Montreal, Que., Canada); corning easy wash polystyrene microtiter plates were bought from Canlab (Montreal, Que., Canada); o-methylisourea hydrochloride was obtained from Lancaster Laboratories (Windham, N.H., USA); alkaline phosphatase conjugated to goat anti-rabbit IgGs was from Pierce Chemical Co. (Rockford, Ill., USA); bovine serum albumin fraction V initial fractionation by cold alcohol precipitation (BSA), complete and incomplete Freund's adjuvants, diethanolamine, 1-methyxanthine, p-nitrophenol phosphate disodium salt, o-phenylenediamine hydrochloride; porcine skin gelatin, rabbit serum albumin (RSA); Sephadex™ G25 fine, Tween™ 20 and ligands used for testing antibodies cross reactivities were obtained from Sigma Chemical Co. (St. Louis, Mo., USA). Whatman™ DE52 diethylaminoethyl-cellulose was obtained from Chromatographic Specialties Inc. (Brockville, Ont., Canada). Dioxane was obtained from A&C American Chemicals Ltd. (Montreal, Que., Canada) and was refluxed over calcium hydride for 4 hours and distilled before use. Other reagents used were of analytical grade.

Synthetic procedures

The synthetic route for the production of AAMU-hemisuccinic acid (VIII) and 1-methyxanthine-8-propionic acid (IX) is presented in FIG. 1.

Synthesis of 2-methoxy-4-imino-6-oxo-dihydropyridine (III)

Compound III is synthesized according to the procedure of Pfeiderer (Pfeilderer, W. (1957) *Chem. Ber.*, 90:2272–2276) as follows. 12.2 g of o-methylisourea hydrochloride (110.6 mmol), 11.81 mL methylcyanoacetate (134 mmol), 12.45 g of sodium methoxide (230.5 mmol) and 80 mL of methanol are placed in a 250 mL round bottom flask. The suspension is stirred and refluxed for 5 hours at 68°–70° C. After cooling at room temperatute, the suspension is filtered through a sintered glass funnel (Pyrex, 40–60 ASTM, 60 mL), and the NaCl on the filter is washed with methanol. The filtrate is filtered by gravity through a Whatman™ no. 1 paper in a 500 mL round bottom flask, and the solvent is evaporated under reduced pressure with a rotary evaporator at 50° C. The residue is solubilized with warm distilled water, and the product is precipitatedd by acidification to pH 3–4 with glacial acetic acid. After 2 hours (or overnight) at room temperature, the suspension is filtered under vacuum through a sintered glass funnel (Pyrex, 40–60 ASTM, 60 mL). The product is washed with water, acetone, and dried. The product is recrystallized with water as the solvent and using charcoal for decolorizing (activated carbon, Norit' A<100 mesh, decolorizing). The yield is 76%.

Synthesis of 1-methyl-2-methoxy-4-imino-6-oxo-dyhydropyrimidine (IV)

Compound IV is synthesized according to the procedure of Pfeiderer (Pfeilderer, W. (1957) *Chem. Ber.*, 90:2272–2276) as follows. 11 g of compound III (77.0 mmol) and 117 mL of 1N NaOH (freshly prepared) are placed in a 250-mL round bottomed flask. The solution is stirred and cooled at 15° C., using a water bath and crushed ice. 11.7 mL dimethylsulfate (123.6 mmol) are added dropwise with a pasteur pipette over a period of 60 min. Precipitation eventaully occurs upon the addition. The suspension is stirred at 15° C. for 3 hours and is left at 4° C. overnight. The product is recovered by filtration under vacuum through a sintered glass funnel (Pyrex, 40–60 ASTM, 60 mL). The yield is 38%.

Synthesis of 1-methyl-4-iminouracil (V)

Compound V was synthesized according to the procedure of Pfeiderer (Pfeilderer, W. (1957) *Chem. Ber.*, 90:2272–2276) as follows. 11.26 g of compound IV (72.6 mmol) and 138 mL 12N HCl are placed in a 250-mL round bottom flask, and the suspension is stirred at room temperature for 16–20 hours. The suspension is cooled on crushed ice, the product is recovered by filtration under vacuum through a sintered glass funnel (Pyrex, 40–60 ASTM, 60 mL). The product is washed with water at 4° C., using a pasteur pipette, until the pH of filtrate is around 4 (about 150 mL). The product is washed with acetone and dried. The yield is 73%.

Synthesis of 1-methyl-4-imino-5-nitrouracil (VI)

Compound VI is synthesized according to the procedure of Lespagnol et al (Lespagnol, A. et al.(1970) Chim. Ther., 5:321–326) as follows. 6.5 g of compound V (46 mmol) and 70 mL of water are placed in a 250 mL round bottom flask. The suspension is stirred and refluxed at 100° C. 6.5 g sodium nitrite (93.6 mmol) is dissolved in 10 mL water and is added gradually to the reaction mixture with a pasteur pipette. 48 mL of glacial acetic acid is added with a pasteur pipette. Upon addition, precipitation occurs and the suspension becomes purple. The suspension is stirred and heated for an additional 5 min., and cooled at room temperature and then on crushed ice. The product is recovered by filtration under vacuum through a sintered glass funnel (Pyrex, 10–15 ASTM, 60 mL). It is washed with water at 4° C. to remove acetic acid and then with acetone. Last traces of acetic acid and acetone are removed under a high vacuum. The yield is 59%.

Synthesis of 1-methyl-4,5-diaminouracil (VII)

Compound VII is synthesized by the procedure of Lespagnol et al. (Lespagnol, A. et al.(1970) Chim. Ther., 5:321–326) as follows. Place 2 g of compound VI (11.7 mmol) and 25 mL water in a 100 mL round bottom flask. Stir the suspension and heat in an oil bath at 60° C. Add gradually 88% sodium hydrosulfite (40.4 mmol), using a spatula, until the purple color disappears (approximately 5 g or 24.3 mmol). Heat for an additional 15 min. Cool the flask on crushed ice and leave at 4° C. overnight. Recover the product by filtration under vacuum through a sintered glass funnel (Pyrex, 30–40 ASTM, 15 mL). Wash the product with water and acetone, and dried. Last traces of acetone are removed under a high vacuum. The yield is 59%.

Synthesis of AAMU-hemisuccinic acid (VIII)

0.30 g of compound VII (1.92 mmol) and 5 mL water are placed in a 20-mL beaker. The suspension is stirred and the pH is adjusted between 8 to 9 with a 3N NaOH solution. 0.33 g succinic anhydride (3.3 mmol) is added to the resulting solution, and the mixture is stirred until the succinic anhydride is dissolved. During this process, the pH of the solution is maintained between 8 and 9. The reaction is completed when all the succinic anhydride is dissolved and the pH remains above 8. The hemisuccinate is precipitated by acidification to pH 0.5 with 12N HCl. The product is recovered by filtration on a Whatman™ No. 1 paper, washed with water to remove HCl. It is then washed with acetone and dried.

Other AAMU or AFMU derivatives

Figure 2:
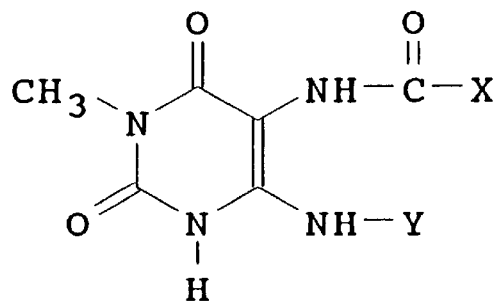
FIGS. 2, 3, 4, and 5 show other AAMU and 1X derivatives which can be used for raising antibodies in accordance with another embodiment of the present invention.
Figure 2:
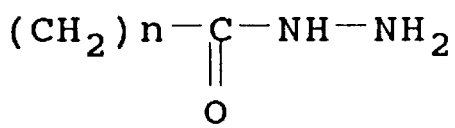
Figure 2:
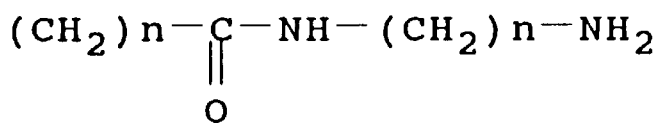
Figure 3:
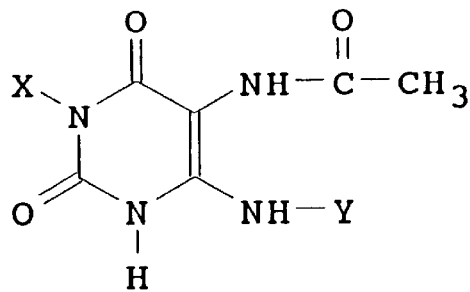
Figure 3:
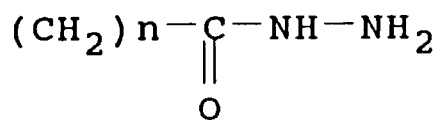
Figure 3:
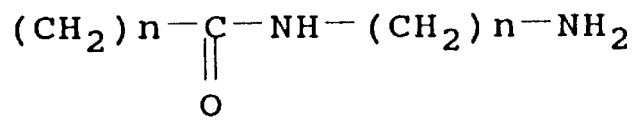

The derivatives shown in FIGS. 2 and 3 can also be used for raising antibodies against AAMU or AFMU that can be used for measuring the concentrations of these caffeine metabolites in urine samples.

Synthesis of 1-methylxanthine-8-propionic acid (IX)

This product is synthesized according to a modified procedure of Lespagnol et al. (Lespagnol, A. et al.(1970) Chim. Ther., 5:321–326) as follows. 0.2 g of compound VIII (0.78 mmol) is dissolved in 2–3 mL of a 15% NaOH solution. The resulting solution is stirred at 100° C. until all of the solvent is evaporated, and is then maintained at this temperature for an additional 5 min. The resulting solid is cooled at room temperature, and dissolved in 10 mL water. The product is precipitated by acidification to pH 2.8 with 12N HCl. After cooling at 4° C. for 2.5 hours, the product is recovered by filtration on a Whatman™ No. 1 paper, washed with water and acetone, and dried. It is recrystallized from water-methanol (20:80, v/v), using charcoal to decolorize the solution.

Other derivatives of 1X

Figure 4:
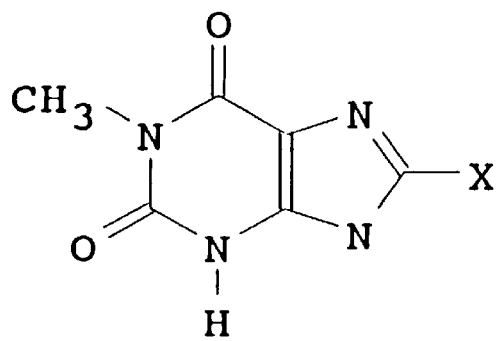
Figure 4:
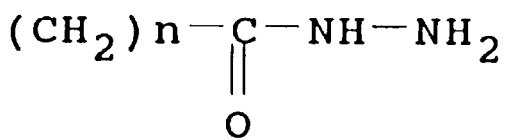
Figure 4:
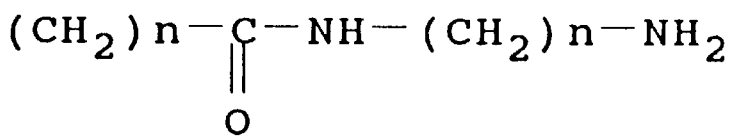
Figure 4:
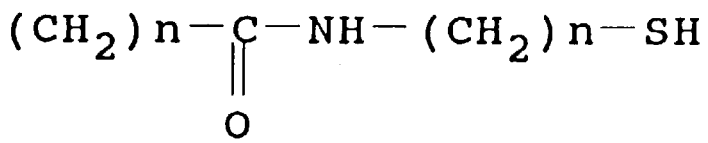
Figure 5:
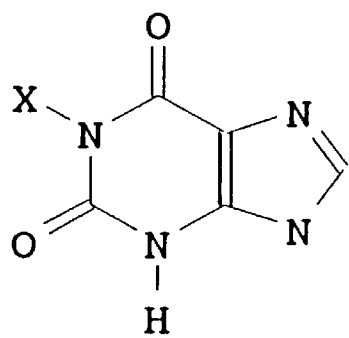
Figure 5:
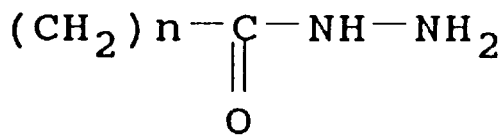
Figure 5:
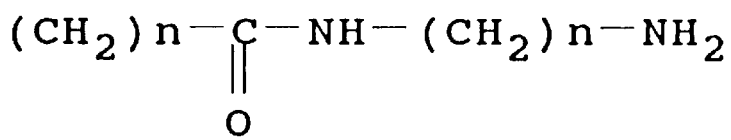
Figure 5:
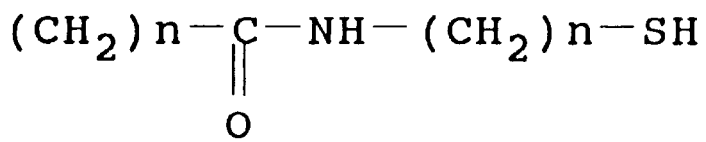

The other derivatives of 1X, shown in FIGS. 4 and 5, can also be used for raising antibodies against 1X and thereby to allow the development of an ELISA for measuring 1X concentration in urine samples.

Synthesis of AAMU

AAMU is synthesized from compound VII according to the procedure of Fink et al (Fink, K. et al. (1964) J. Biol. Chem., 249:4250–4256) as follows. 1.08 g of compound VII (6.9 mmol) and 20 mL acetic acid anhydride were placed in a 100-mL round bottom flask. The suspension is stirred and refluxed at 160°–165° C. for 6 min. After cooling at room temperature, the suspension is filtered under vacuum through a sintered glass funnel (Pyrex, 10–15 ASTM, 15 mL). The product is washed with water and acetone, and dried. The product is recrystallized in water.

NMR spectroscopy $^1$H and $^{13}$C NMR spectra of compounds VIII and IX are obtained using a 500 MHz spectrophotometer (Variant™ XL 500 MHz, Varian Analytical Instruments, San Fernando, Calif., USA) using deuterated dimethyl sulfoxide as solvent.

Conjugation of haptens to bovine serum albumin and rabbit serum albumin

The AAMU-hemisuccinic acid (VIII) and the 1-methyxanthine propionic acid (IX) are conjugated to BSA and RSA according to the following mixed anhydride method. Place 31.7 mg of compound VIII (0.12 mmol) or 14.9 mg of compound IX (0.06 mmol) in a 5-mL round bottom flask. Pipet 52.2 μL of tri-n-butylamine (0.24 mmol) and 900 μL of dioxane dried over calcium hydride and freshly distilled. Cool at 10° C. in a water bath using crushed ice. Pipet 12.6 μL isobutyl chloroformate at 4° C. (0.12 mmol, recently purchased or opened) and stir for 30–40 min at 10°–12° C. While stirring, dissolve 70 mg BSA or RSA (0.001 mmmol) with 1.83 mL water in a glass tube, add 1.23 mL dioxane freshly dried and distilled, and cool the BSA or RSA solution on ice. After 30–40 min of the above stirring, 70 μL of 1N NaOH solution cooled on ice is added to the BSA or RSA solution and the resulting solution is poured in one portion to the flask. Stir the solution at 10°–12° C. for 3 hours and dialyze against 1 liter water for 2 days at room temperature, with water changed twice a day. Determine the protein concentration of the conjugates and the amounts moles of AAMU or 1X incorporated moles of BSA or RSA by methods described below and store them as 1 mL aliquots at −20° C.

Protein determination by the method of Lowry et al (Lowry, O. H. et al. (1951) J. Biol. Chem., 193:265–275)

A) Solutions

Solution A: 2 g $Na_2CO_3$ is dissolved in 50 mL water, 10 mL of 10% SDS and 10 mL 1 NaOH, water to 100 mL. Freshly prepared.

Solution B: 1% NaK Tartrate

Solution C: 1% $CuSO_4.5H_2O$

Solution D: 1N phenol (freshly prepared): 3 mL Folin & Ciocalteu's phenol reagent (2.0N) and 3 mL water.

Solution F: 98 mL Solution A, 1 mL Solution B, 1 mL Solution C. Freshly prepared.

BSA: 1 mg/mL. 0.10 g bovine serum albumin (fraction V)/100 mL.

B) Assay

| Standard curve | Tubes # (13 × 100 mm) | | | | | | |
|---|---|---|---|---|---|---|---|
| Solution | 1 | 2 | 3 | 4 | 5 | 6 | 7 |
| BSA (µL) | 0 | 10 | 15 | 20 | 30 | 40 | 50 |
| Water (µL) | 200 | 190 | 185 | 180 | 170 | 160 | 150 |
| Solution F (mL) | 2.0 | 2.0 | 2.0 | 2.0 | 2.0 | 2.0 | 2.0 |
| Vortex and leave 10 min at room temperature. | | | | | | | |
| Solution D (µL) | 200 | 200 | 200 | 200 | 200 | 200 | 200 |
| Vortex and leave at room temperature for 1 hour. Read absorbance at 750 mm using water as the blank. | | | | | | | |

| Unknown | | Tube # (13 × 100 mm) | | |
|---|---|---|---|---|
| Solution | D.F.ª | 1 | 2 | 3 |
| Unknown (µL) | ? | x | x | x |
| Water (µL) | | y | y | y    x + y = 200 µL |
| Solution F (mL) | | 2.0 | 2.0 | 2.0 |
| Vortex and leave 10 min at room temperature | | | | |
| Solution D (µL) | | 200 | 200 | 200 |

Vortex and leave 1 hour at room temperature Read absorbances at 750 nm using water as the blank. Calculate the protein concentration using the standard curve and taking account of the dilution factor (D.F.). a, D.F. (dilution factor). It has to be such so that the absorbance of the unknown at 750 nm is within the range of absorbance of the standards. Method to determine the amounts of moles of AAMU or 1X incorporated per mole of BSA or RSA.

This method gives an approximate estimate. It is a useful one because is allow to determine whether the coupling as proceeded as expected.

A) Solutions

10% sodium dodecyl sulfate (SDS)

1% SDS solution 0.5 or 1 mg/mL of AAMU-BSA (or AAMU-RSA) in a 1% SDS solution (1 mL).

0.5 or 1 mg/mL of AAMU-BSA (or AAMU-RSA) in a 1% SDS solution (1 mL)

0.5 or 1 mg/mL of BSA or RSA in a 1% SDS solution (1 mL).

B) Procedure

Measure the absorbance of the AAMU conjugate solution at 265 nm, with 1% SDS solution as the blank.

Measure the absorbance of the BSA (or RSA) solution at 265 nm, with 1% SDS solution as the blank.

Calculate the amount of mole of AAMU incorporated per mole of BSA (or RSA) with this formula.

$$y = \frac{A_{265}(AAMU\text{-}BSA) - A_{265}(BSA)}{\epsilon_{265}(AAMU) \times [BSA]}$$

Where:

y is the amount of mole of AAMU/mole of BSA (or RSA)

$\epsilon_{265}$ (AAMU) is the extinction coefficient of AAMU=$10^4$ $M^{-1}cm^{-1}$.

[BSA]=BSA (mg/mL)/68,000/mmole.

To calculate the amount of mole of 1x incorporated per mole of BSA or RSA, use the same procedure but with this formula.

$$y = \frac{A_{252}(1X\text{-}BSA) - A_{252}(BSA)}{\epsilon_{252}(1X) \times [BSA]}$$

Where:

y is the amount of mole of 1X/mole of BSA (or RSA) $\epsilon_{252}$ (AAMU) is the extinction coefficient of 1X=$10^4$ $M^{-1}cm^{-1}$.

[BSA]=BSA (mg/mL)/68,000/mmole.

Coupling of haptens to horse radish peroxidase

The AAMU derivative (VIII) and 1X derivative (IX) are conjugated to horse radish peroxidase (HRP) by the following procedure. Place 31.2 mg of compund VIII (or 28.3 mg of compound IX) in a 5 mL round bottom flask. Pipet 500 µL of dioxane freshly dried over calcium chloride. Stir the suspension and cool at 10° C. using a water bath and crushed ice. Pipet 114 µL tributylamine and 31 µL of isobutyl chloroformate (recently opened or purchased). Stir for 30 min. at 10° C. While stirring, dissolve 13 mg of horse radish peroxidase (HRP) in 2 mL of water and cool the solution at 4° C. on crushed ice. After the 30 min. stirring, pipet 100 µL of a 1N NaOH solution at 4° C. to the HRP solution and pour the alkaline HRP solution at once in the 5 mL flask. Stir the suspension 4 hours at 10°–12° C. Separate the free derivative from the HRP conjugate by filtration on Sephadex G-25™ column (1.6×30 cm) equilibrated and eluted with a 0.05M sodium phosphate buffer, pH 7.5. Collect fractions of 1.0–1.2 mL with a fraction collector. During the elution two bands are observed: the HRP conjugate band and a light yellow band behind the HRP conjugate band. The HRP conjugate elutes between fractions 11–16. Pool fractions containing the HRP conjugate in a 15-mL tisssue culture tube with a screw cap. Determine the HRP conjugate concentration at 403 nm after diluting an aliquot (usually 50 µL+650 µL of buffer).

$$[\text{HRP-conjugate}](mg/mL) = A_{403} \times 0.4 \times D.F.$$

Record the ultraviolet (UV) absorption spectrum between 320 and 220 nm. The presences of peaks at 264 and 270 nm for AAMU-HRP and 1X-HRP conjugates, respectively, are indicative that the couplings proceeded as expected.

After the above measurements, 5 µL of a 4% thiomersal solution is added per mL of the AAMU-HRP or 1X-HRP comjugate solution. The conjugates are stored at 4° C.

Antibody production

Four mature females New Zealand white rabbits (Charles River Canada, St-Constant, Que., Canada) were used for antibody production. The protocol employed in this study was approved by the McGill University Animal Care Committee in accordance with the guidelines from the Canadian Council on Animal Care.

An isotonic saline solution (0.6 mL) containing 240 mg of BSA conjugated antigen was emulsified with 0.6 mL of a complete Freund's adjuvant. 0.5 mL of the emulsion (100 mg of antigen) was injected per rabbit intramuscularly or subcutaneously. Rabbits were subsequently boosted at intervals of three weeks with 50 mg of antigen emulsified in incomplete Freund's adjuvant. Blood was collected by venipuncture of the ear 10–14 days after boosting. Antisera were stores at 4° C. in the presence of 0.01% sodium azide.

Double immunodiffusion in agar plate

An 0.8% agar gel in PBS was prepared in a 60×15 mm petri dish. Rabbit serum albumin (100 µL of 1 mg mL$^{-1}$) conjugated to AAMU (or 1X) was pipetted in the center well, and 100 µL of rabbit anitiserum was pipetted in peripheral wells. The immunodiffusion was carried out in a humidified chamber at 37° C. overnight and the gel was inspected visually.

Antiserum titers

The wells of a microtiter plate were coated with 10 μg mL$^{-1}$ of rabbit serum albumin-AAMU (or 1X) conjugate in sodium carbonate buffer, pH 9.6) for 1 hour at 37° C. (100 μL/per well). They were then washed three times with 100 μL TPBS (phosphate buffer saline containing 0.05% Tween™ 20) and unoccupied sites were blocked by an incubation with 100 mL of TPBS containing 0.05% gelatin for 1 hour at 37° C. The wells were washed three times with 100 μL TPBS and 100 μL of antiserum diluted in TPBS was added. After 1 hour at 37° C., the wells were washed three times with TPBS, and 100 μL of goat anti-rabbit IgGs-alkaline phosphatase conjugate diluted in PBS containing 1% BSA was added. After 1 hour at 37° C., the wells were washed three times with TPBS and three times with water. To the wells were added 100 μL of a solution containing $MgCl_2$ (0.5 mM) and p-nitrophenol phosphate (3.85 mM) in diethanolamine buffer (10 mM, pH 9.8). After 30 min. at room temperature, the absorbency was read at 405 nm with a micro-plate reader. The antibody titer is defined as the dilution required to change the absorbance by one unit (1 au).

Isolation of rabbit IgGs

The DE52-cellulose resin was washed three times with sodium phosphate buffer (500 mM, pH 7.50), the fines were removed and the resin was equilibrated with a sodium phosphate buffer (10 mM, pH 7.50). The resin was packed in a 50×1.6 cm column and eluted with 200–300 mL equilibrating buffer before use. To antiserum obtained from 50 mL of blood (30–32 mL) was added drop-wise 25–27 mL 100% saturated ammonium sulfate solution with a Pasteur pipette. The suspension was left at room temperature for 3 h and centrifuged for 30 min. at 2560 g at 20° C. The pellet was dissolved with 15 mL sodium phosphate buffer (10 mM, pH 7.50) and dialyzed at room temperature with the buffer changed twice per day. The dialyzed solution was centrifuged at 2560 g for 10 min. at 20° C. to remove precipitate formed during dialysis. The supernatant was applied to the ion-exchange column. Fractions of 7 mL were collected. After application, the column is eluted with the equilibrating buffer until the absorbance at 280 nm become less than 0.05 au. It is then eluted with the equilibrating buffer containing 50 mM NaCl. Fractions having absorbencies greater than 0.2 at 280 nm are saved and stored at 4° C. Protein concentrations of the fractions are determined as described above.

Competitive antigen ELISA

Buffers and water without additives were filtered through millipore filters and kept for 1 week. BSA, antibodies, Tween™ 20 and horse radish peroxidase conjugates were added to these buffers and water just prior to use. Urine samples were usually collected 4 hours after drinking a cup of coffee (instant or brewed with approximately 100 mg of caffeine per cup) and stored at −80° C. They were diluted 10 times with sodium phosphate buffer (620 mosm, pH 7.50) and were subsequently diluted with water to give concentrations of AAMU and 1X no higher than 3×10$^{-6}$M in the ELISA. All the pipettings were done with an eight-channel pipette, except those of the antibody and sample solutions. Starting with the last well, 100 μL of a carbonate buffer (100 mM, pH 9.6) containing 2.5 μg mL$^{-1}$ antibodies was pipetted. After 90 min. at room temperature, the wells were washed three times with 100 mL of TPB: isotonic sodium phosphate buffer (310 mosm, pH 7.50) containing 0.05% Tween™ 20.

After the initial wash, unoccupied sites were blocked by incubation for 90 min. at room temperature with 100 μL TPB containing 3% BSA. The wells were washed four times with 100 μL TPB. This was followed by additions of 50 mL of 12 mg mL$^{-1}$ AAMU-HRP or 1X-HRP conjugate in 2×TPB containing 2% BSA, and 50 μL of either water, standard (13 standards; AAMU or 1X, 2×10$^{-4}$ to 2×10$^{-8}$M) or sample in duplicate. The microplate was gently shaken with an orbital shaker at room temperature for 3–4 hours. The wells were washed three times with 100 μL with TPB containing 1% BSA and three times with water containing 0.05% Tween 20. To the washed plate was added 150 μL of a substrate buffer composed of citric acid (25 mM) and sodium phosphate dibasic buffer (50 mM, pH 5.0) containing 0.06% hydrogen peroxide and 0.04% o-phenylenediamine hydrochloride. After 20 min. at room temperature with shaking, the reaction was stopped with 50 μL of 2.5M HCl. After shaking the plate 3 min., the absorbances were read with a microtiter plate reader at 490 nm.

Results

Polyclonal antibodies against AAMU and 1X could be successfully raised in rabbits after their conjugation to bovine serum albumin. Each rabbit produced antibody titers of 30,000–100,000 as determined by ELISA. This was also indicated by strong precipitin lines after double immunodiffusion in agar plates of antisera and derivatives conjugated to rabbit serum albumin. On this basis, a) IgGs antibodies were isolated on a DE-52 cellulose colunmn and b) a competitive antigen ELISA for NAT2 phenotyping using caffeine as probe drug was developed according to the methods described in the above section entitled Materials and Methods.

Contrary to current methods used for phenotyping, the assay involves no extraction, is sensitive and rapid, and can be readily carried out on a routine basis by a technician with a minimum of training in a clinical laboratory.

The present invention will be more readily understood by referring to the following examples which are given to illustrate the invention rather than to limit its scope.

EXAMPLE I

A Competitive Antigen ELISA for NAT2 Phenotyping using Caffeine as a Probe Drug

Buffers and water without additives were filtered through millipore filters and kept for 1 week. BSA, antibodies, Tween™ 20 and horse radish peroxidase conjugates were added to these buffers and water just prior to use. Urine samples were usually collected 4 hours after drinking a cup of coffee (instant or brewed with approximately 100 mg of caffeine per cup) and stored at −80° C. They were diluted 10 times with sodium phosphate buffer (620 mosm, pH 7.50) and were subsequently diluted with water to give concentrations of AAMU and 1X no higher than 3×10$^{-6}$M in the ELISA. All the pipettings were done with an eight-channel pipette, except those of the antibody and sample solutions. Starting with the last well, 100 μL of a carbonate buffer (100 mM, pH 9.6) containing 2.5 μg mL$^{-1}$ antibodies was pipetted. After 90 min. at room temperature, the wells were washed three times with 100 mL of TPB: isotonic sodium phosphate buffer (310 mosm, pH 7.50) containing 0.05% Tween™ 20.

After the initial wash, unoccupied sites were blocked by incubation for 90 min. at room temperature with 100 μL TPB containing 3% BSA. The wells were washed four times with 100 μL TPB. This was followed by additions of 50 mL of 12 mg mL$^{-1}$ AAMU-HRP or 1X-HRP conjugate in 2×TPB containing 2% BSA, and 50 μL of either water, standard (13 standards; AAMU or 1X, 2×10$^{-4}$ to 2×10$^{-8}$M) or sample in duplicate. The microplate was gently shaken with an orbital shaker at room temperature for 3–4 hours. The wells were washed three times with 100 μL with TPB containing 1% BSA and three times with water containing 0.05% Tween 20. To the washed plate was added 150 μL of a substrate buffer composed of citric acid (25 mM) and sodium phosphate dibasic buffer (50 mM, pH 5.0) containing 0.06% hydrogen peroxide and 0.04% o-phenylenediamine hydrochloride. After 20 min. at room temperature with shaking, the reaction was stopped with 50 μL of 2.5M HCl. After shaking the plate 3 min., the absorbances were read with a microtiter plate reader at 490 nm.

The competitive antigen ELISA curves of AAMU-Ab and 1X-Ab determinations obtained in duplicate are presented in FIG. 6. Each curve represents triplicate determinations in a single run. The error bars represent standard deviations. For data point with no error bars, the error bars are less the size of the symbol. Under the experimental conditions of the ELISA: background was less than 0.10 au; the practical limits of detection of AAMU and 1X were $2 \times 10^{-7}$M and $2 \times 10^{-6}$M, respectively, concentrations 500 and 50 times lower than those in urine samples from previous phenotyping studies (Kilbane, A. J. et al. (1990) Clin. Pharmacol. Ther., 47:470–477); the intra-assay and interassay coefficients of variations of AAMU and 1X were 15–20% over the concentration range of 0.01–0.05 mM.

A variety of conditions for the ELISA were tested and a number of noteworthy observations were made: gelatin, which was used in the competitive antigen ELISA determination of caffeine in plasma (Fickling, S. A. et al. (1990) J. Immunol. Meth., 129:159–164), could not be used in our ELISA owing to excessive background absorbency which varied between 0.5 and 1.0 au; in the absence of Tween™ 20, absorbency changes per 15 min. decreased by a factor of at least 3, and calibration curves were generally erratic; absorbency coefficients of variation of samples increased by a factor of 3 to 4 when the conjugates and haptens were added to the wells as a mixture instead individually.

The cross reactivities of AAMU-Ab and 1X-Ab were tested using a wide variety of caffeine metabolites and structural analogs (Table 1 below). AAMU-Ab appeared highly specific for binding AAMU, while 1X-Ab appeared relatively specific for binding 1X. However, a 11% cross reactivity was observed with 1-methyluric acid (1U), a major caffeine metabolite.

TABLE 1

Cross-reactivity of AAMU-Ab and 1X-Ab towards different caffeine metabolites and structural analogs

| Compound | % Cross-Reaction | |
|---|---|---|
| | AAMU-Ab | 1X-Ab |
| Xanthine | 0[a] | 0 |
| Hypoxanthine | 0 | 0 |
| 1-Methyl Xanthine (1X) | 0 | 100 |
| 3-Methyl Xanthine | 0 | 0 |
| 7-Methyl Xanthine | 0 | 0 |
| 8-Methyl Xanthine | 0 | 0 |
| 1,3-Dimethyl Xanthine (Theophylline) | 0 | 0.2 |
| 1,7-Dimethyl Xanthine (Paraxanthine) | 0 | 0.5 |
| 3,7-Dimethyl Xanthine (Theobromine) | 0 | 0 |
| 1,3,7-Trimethyl Xanthine (Caffeine) | 0 | 0 |
| Uric acid | 0 | 0 |
| 1-Methyluric acid | 0 | 11 |
| 1,7-Dimethyluric acid | 0 | 0 |
| Guanine | 0 | 0 |
| Uracil | 0 | 0 |
| 5-Acetamino-6-amino-uracil | 0.6 | 0 |
| 5-Acetamino-6-amino-1-methyluracil (AAMU) | 100 | 0 |
| 5-Acetamino-6-amino-1,3-dimethyluracil | 0 | 0 |

[a]The number 0 indicates either an absence of inhibition or an inhibition no higher than 40% at the highest compound concentration tested in the ELISA ($5 \times 10^{-3}$M); concentrations of 5-acetamino-6-amino-1-methyluracil (AAMU) and 1-Methyl Xanthine (1X) required for 50% inhibition in the competitive antigen ELISA were $1.5 \times 10^{-6}$M and $10^{-5}$M, respectively.

The relative high level of cross reactivity of 1U is, however, unlikely to interfere significantly in the determination of 1X and the assignment of NAT2 phenotypes, since the ratio of 1U:1X is no greater than 2.5:1 in 97% of the population (Tang, B-K. et al. (1991) Clin. Pharmacol. Ther., 49:648–657). This is confirmed by measurements of apparent concentrations of 1X when the ratio varied between 0–8.0 at the fixed 1X concentration of $3 \times 10^{-6}$M (Table 2 below). At 1U:1X ratios of 2.5 and 3.0, the apparent increases were 22% and 32%, respectively.

TABLE 2

The effect of the ratio 1U:1X on the determination of 1X concentration by ELISA at fixed 1X concentration of $3 \times 10^{-6}$M

| 1U:1X ratio | $[1X] \times 10^6$(M) |
|---|---|
| 0.0 | 3.00 |
| 0.50 | 2.75 |
| 1.00 | 3.25 |
| 1.50 | 3.25 |
| 2.00 | 3.60 |
| 2.50 | 3.65 |
| 3.00 | 3.95 |
| 4.00 | 4.20 |
| 5.00 | 4.30 |
| 6.00 | 4.50 |
| 8.00 | 4.30 |

The following observations attested to the validity of the competitive antigen ELISA for NAT2 phenotyping.

1) The ELISA assigned the correct phenotype in 29 of 30 individuals that have been phenotyped by capillary electrophoresis (CE) (Lloyd, D. et al. (1992) J. Chrom., 578:283–291).

2) In the CE method, the phenotype was determined using AFMU/1X peak height ratios rather than the AAMU/1X molar ratios used in the ELISA. When the molar ratios determined by ELISA and the peak height ratios determined by CE were correlated by regression analysis, the calculated regression equation was y=0.48+0.87 x, with a correlation coefficient (r) of 0.84. Taking account that these two ratios are not exactly equal and that Kalow and Tang (Kalow, W. et al. (1993) Clin. Pharmacol. Ther., 53:503–514) have pointed out that using AFMU rather than AAMU can lead to misclassification of NAT2 phenotypes, there is a remarkable agreement between the two methods.

3) The ELISA was used in determining the NAT2 phenotype distribution within a group of 48 individuals (FIG. 7). This histogram was obtained with a group of 48 individuals (FIG. 7). Assuming an antimode of 1.80, the test population contained 60.4% slow acetylators and 39.6% fast acetylators. This is consistent with previously reported distributions (Kalow, W. et al. (1993) *Clin. Pharmacol. Ther.*, 53:503–514; Kilbane, A. J. et al. (1990) *Clin. Pharmacol. Ther.*, 47:470–477).

EXAMPLE II

Determination of 5-acetamino-6-amino-1-methyluracyl (AAMU) and 1-methyl xanhtine in Urine Samples with the ELISA Kit

TABLE 3

Content of the ELISA kit and conditions of storage

| Item | Unit | State | Amt | Storage conditions |
|---|---|---|---|---|
| Tween 20 | 1 vial | Liquid | 250 μL/vial | 4° C. |
| $H_2O_2$ | 1 vial | Liquid | 250 μL/vial | 4° C. |
| AAMU-HRP | 1 vial | Liquid | 250 μL/vial | 4° C. |
| 1X-HRP | 1 vial | Liquid | 250 μL/vial | 4° C. |
| Buffer A | 4 vials | Solid | 0.8894 g/vial | 4° C. |
| Buffer B | 6 vials | Solid | 1.234 g/vial | 4° C. |
| Buffer C | 6 vials | Solid | 1.1170 g/vial | 4° C. |
| Buffer D | 6 vials | Solid | 0.8082 g/vial | 4° C. |
| Plate(AAMU-Ab) | 2 | Solid | — | 4° C. |
| Plate(1X-Ab) | 2 | Solid | — | 4° C. |
| Buffer E | 6 vials | Solid | 0.9567 g/vial | -20° C. |
| Standards (AAMU) | 14 vials | Liquid | 200 μL | -20° C. |
| Standards(1X) | 14 vials | Liquid | 200 μL | -20° C. |
| 1N NaOH | 1 bottle | Liquid | 15 mL | 20° C. |
| 1N HCl | 1 bottle | Liquid | 15 mL | 20° C. |

Conversion of AFMU to AAMU

In order to determine the AAMU concentrations in urine samples by competitive antigen ELISA, a transformation of AFMU to AAMU is required.

Thaw and warm up to room temperature the urine sample.

Suspend the sample thoroughly with the vortex before pipeting.

Pipet 100 μL of a urine sample in a 1.5 mL-microtube.

Pipet 100 μL of a 1N NaOH solution.

Leave at room temperature for 10 min.

Neutralize with 100 μL 1N HCl solution.

Pipet 700 μL of Buffer A (dissolve the powder of one vial A/50 mL).

Dilutions of Urine Samples for the Determinations of [AAMU] and [1X] by ELISA

The dilutions of urine samples required for determinations of AAMU and 1X are a function of the sensitivity of the competitive antigen ELISA and AAMU and 1X concentrations in urine samples. It is suggested to dilute the urine samples by a factor so that AAMU and 1X concentrations are about $3 \times 10^{-6}$M in the well of the microtiter plate. Generally, dilution factors of 100–400 and 50–100 have been used for AAMU and 1X, respectively.

TABLE 4

| | Microtube # | | | | | | | |
|---|---|---|---|---|---|---|---|---|
| Dilution Factor | 20× | 40× | 50× | 80× | 100× | 150× | 200× | 400× |
| Solution | 1 | 2 | 3 | 4 | 5 | 6 | 7 | 8 |
| Urine sample (mL)[a] 10 × diluted | 500 | 250 | 200 | 125 | 100 | 66.7 | 50 | 25 |
| Buffer B (mL) | 500 | 750 | 800 | 875 | 900 | 933.3 | 950 | 975 |

[a]Vortex the microtubes containing the urine sample before pipeting. Store the diluted urine samples at -20° C. in a styrofoam box for microtubes.

Buffer B: dissolve the content of one vial B/100 mL.

Determination of [AAMU] and [1X] in Diluted Urine Samples by ELISA

Precautions

The substrate is carcinogenic. Wear surgical gloves when handling Buffer E (Substrate buffer). Each sample is determined in duplicate. An excellent pipeting technique is required. When this technique is mastered the absorbance values of duplicate should be within less than 5%. Buffers C, D and E are freshly prepared. Buffer E-$H_2O_2$ is prepared just prior pipeting in the microtiter plate wells.

Preparation of samples:

Prepare Table 5 with a computer and print it. This table shows the content of each well of a 96-well microtiter plate. Enter the name of the urine sample (or number) at the corresponding well positions in Table 5. Select the dilution factor (D.F.) of each urine sample and enter at the corresponding position in Table 5. Enter the dilution of each urine sample with buffer B at the corresponding position in Table 5: for example, for a D.F. of 100 (100 μL of 10× diluted urine sample+900 μL buffer B), enter 100/900. See "Dilutions of urine samples . . ." procedure described above for the preparation of the different dilutions. Prepare the different dilutions of the urine samples in 1.5-mL microtubes using a styrofoam support for 100 microtubes. Prepare Table 6 with a computer and print it. Using a styrofoam support (100 microtubes), prepare the following 48 microtubes in the order indicated in Table 4.

TABLE 5

Positions of blanks, control and urine samples in a microtiter plate

| Sample | Well # | D.F | Dil. | Sample | Well # | D.F | Dil. |
|---|---|---|---|---|---|---|---|
| Blank | 1–2 | – | | Control | 49–50 | – | |
| Control | 3–4 | – | | 7 | 51–52 | | |
| S1 | 5–6 | – | | 9 | 53–54 | | |
| S2 | 7–8 | – | | 10 | 55–56 | | |
| S3 | 9–10 | – | | 11 | 57–58 | | |
| S4 | 11–12 | – | | 12 | 59–60 | | |
| S5 | 13–14 | – | | 13 | 61–62 | | |
| S6 | 15–16 | – | | 14 | 63–64 | | |
| S7 | 17–18 | – | | 15 | 65–66 | | |
| S8 | 19–20 | – | | 16 | 67–68 | | |
| S9 | 21–22 | – | | 17 | 69–70 | | |
| S10 | 23–24 | – | | Control | 71–72 | – | |
| S11 | 25–26 | – | | 18 | 73–74 | | |
| S12 | 27–28 | – | | 19 | 75–76 | | |
| S13 | 29–30 | – | | 20 | 77–78 | | |
| S14 | 31–32 | – | | 21 | 79–80 | | |
| S15 | 33–34 | – | | 22 | 81–82 | | |
| 1 | 35–36 | | | 23 | 83–84 | | |
| 2 | 37–38 | | | 24 | 85–86 | | |
| 3 | 39–40 | | | 25 | 87–88 | | |
| 4 | 41–42 | | | 26 | 89–90 | | |
| 5 | 43–44 | | | 27 | 91–92 | | |
| 6 | 45–46 | | | 28 | 93–94 | | |
| 7 | 47–48 | | | Blank | 95–96 | – | |

TABLE 6

Content of the different microtubes

| Tube # | Sample | Content | Tube # | Sample | Content |
|---|---|---|---|---|---|
| 1 | Blank | Buffer B | 25 | 7 | Dil. Urine |
| 2 | Control | Buffer B | 26 | 8 | Dil. Urine |
| 3 | S1 | AAMU or 1X | 27 | 9 | Dil. Urine |
| 4 | S2 | AAMU or 1X | 28 | 10 | Dil. Urine |
| 5 | S3 | AAMU or 1X | 29 | 11 | Dil. Urine |
| 6 | S4 | AAMU or 1X | 30 | 12 | Dil. Urine |
| 7 | S5 | AAMU or 1X | 31 | 13 | Dil. Urine |
| 8 | S6 | AAMU or 1X | 32 | 14 | Dil. Urine |
| 9 | S7 | AAMU or 1X | 33 | 15 | Dil. Urine |
| 10 | S8 | AAMU or 1X | 34 | 16 | Dil. Urine |
| 11 | S9 | AAMU or 1X | 35 | 17 | Dil. Urine |
| 12 | S10 | AAMU or 1X | 36 | Control | Buffer B |
| 13 | S11 | AAMU or 1X | 37 | 18 | Dil. Urine |
| 14 | S12 | AAMU or 1X | 38 | 19 | Dil. Urine |
| 15 | S13 | AAMU or 1X | 39 | 20 | Dil. Urine |
| 16 | S14 | AAMU or 1X | 40 | 21 | Dil. Urine |
| 17 | S15 | AAMU or 1X | 41 | 22 | Dil. Urine |
| 18 | 1 | Dil. Urine | 42 | 23 | Dil. Urine |
| 19 | 2 | Dil. Urine | 43 | 24 | Dil. Urine |
| 20 | 3 | Dil. Urine | 44 | 25 | Dil. Urine |
| 21 | 4 | Dil. Urine | 45 | 26 | Dil. Urine |
| 22 | 5 | Dil. Urine | 46 | 27 | Dil. Urine |
| 23 | 6 | Dil. Urine | 47 | 28 | Dil. Urine |
| 24 | Control | Buffer B | 48 | Blank | Buffer B |

Solutions:
Buffer C: dissolve the content of one vial C/50 mL. Pipet 25 mL of Tween 20.
Buffer D: dissolve the content of one vial D/25 mL. Pipet 25 mL of Tween 20.
0.05% Tween 20: Pipet 25 $\mu$L of Tween 20 in a 100-mL erlnemeyer flask containing 50 mL of water.
2.5N HCl: 41.75 mL of 12N HCl/200 mL. Store in a 250-mL glass bottle.
AAMU-HRP conjugate: Pipet 9 mL of Buffer C in a 15-mL glass test tube. Pipet 90 $\mu$L of AAMU-HRP stock solution.
1X-HRP conjugate: Pipet 9 mL of the 2% BSA solution in a 15-mL glass test tube. Pipet 90 $\mu$L 1X-HRP stock solution.
Buffer E-$H_2O_2$: Dissolve the content of one vial E-subtrate/50 ml water. Pipet 25 $\mu$L of a 30% $H_2O_2$ solution (prepared just prior pipeting in the microtiter plate wells).

TABLE 7

Standard solutions of AAMU and 1X (diluted with buffer B)

| | AAMU | | 1X |
|---|---|---|---|
| Standard | [AAMU] | Standard | [1X] |
| 1 | $1.12 \times 10^{-4}$M | 1 | $2.00 \times 10^{-4}$M |
| 2 | $6.00 \times 10^{-5}$M | 2 | $1.12 \times 10^{-4}$M |
| 3 | $3.56 \times 10^{-5}$M | 3 | $6.00 \times 10^{-5}$M |
| 4 | $2.00 \times 10^{-5}$M | 4 | $3.56 \times 10^{-5}$M |
| 5 | $6.00 \times 10^{-6}$M | 5 | $2.00 \times 10^{-5}$M |
| 6 | $3.56 \times 10^{-6}$M | 6 | $1.12 \times 10^{-5}$M |
| 7 | $2.00 \times 10^{-6}$M | 7 | $6.00 \times 10^{-6}$M |
| 8 | $1.12 \times 10^{-6}$M | 8 | $3.56 \times 10^{-6}$M |
| 9 | $6.00 \times 10^{-7}$M | 9 | $2.00 \times 10^{-6}$M |
| 10 | $3.56 \times 10^{-7}$M | 10 | $1.12 \times 10^{-6}$M |
| 11 | $2.00 \times 10^{-7}$M | 11 | $6.00 \times 10^{-7}$M |
| 12 | $1.12 \times 10^{-7}$M | 12 | $3.56 \times 10^{-7}$M |
| 13 | $6.00 \times 10^{-8}$M | 13 | $2.00 \times 10^{-7}$M |
| 14 | $3.56 \times 10^{-8}$M | 14 | $1.12 \times 10^{-7}$M |
| 15 | $2.00 \times 10^{-8}$M | 15 | $6.00 \times 10^{-8}$M |

Conditions of the ELISA

Pipet 50 $\mu$L/well of AAMU-HRP (or 1X-HRP) conjugate solution, starting from the last row. Pipet 50 $\mu$L/well of diluted urine samples in duplicate, standards, blank with a micropipet (0–200 $\mu$L), starting from well #96 (see Table 5). Cover the plate and mix gently by vortexing for several seconds. Leave the plate at room temperature for 3 h. Wash 3 times with 100 $\mu$L/well with buffer C, using a microtiter plate washer. Wash 3 times with 100 $\mu$L/well with the 0.05% tween 20 solution. Pipet 150 $\mu$L/well of Buffer E-$H_2O_2$ (prepared just prior pipeting in the microtiter plate wells). Shake 20–30 min at room temperature with an orbital shaker. Pipet 50 $\mu$L/well of a 2.5N HCl solution. Shake 3 min with the orbital shaker at room temperature. Read the absorbance of the wells with microtiter plate reader at 490 nm. Print the sheet of data and identify properly the data sheet.

Calculation of the [AAMU] and [1X] in Urine Samples from the Data

Draw a Table 5 with a computer. Using the data sheet of the microtiter plate reader, enter the average absorbance values of blanks, controls (no free hapten present), standards and samples in Table 6. Draw the calibration curve on a semi-logarithmic plot (absorbance at 490 nm as a function of the standard concentrations) using sigma plot (or other plot software). Find the [AAMU] (or [1X]) in the microtiter well of the unknown from the calibration curve and enter the data in Table 6. Multiply the [AAMU] (or [1X]) of the unknown by the dilution factor and enter the result in the corresponding case of Table 6.

TABLE 8

Composition of the different buffer

| Buffer | pH | Composition | Concen. (mM) | [P] (mM) |
|---|---|---|---|---|
| A | 7.50 | 0.15629 g/100 mL $NaH_2PO_4$ | 11.325 | 71.424 |
| | | 1.622 g/100 mL $Na_2HPO_4.7H_2O$ | 60.099 | |
| | | 1.778 g/100 mL (total weight) | | |
| B | 7.50 | 0.1210191 g/100 mL $NaH_2PO_4$ | 8.769 | 49.999 |
| | | 1.11309 g/100 mL of $Na_2HPO_4.7H_2O$ | 41.23 | |
| | | 1.2341 g/100 mL (total weight) | | |
| C | 7.50 | 1 g/100 mL of BSA | — | |
| | | 0.1210191 g/100 mL of $NaH_2PO_4$ | 8.769 | 49.999 |
| | | 1.11309 g/100 mL of $Na_2HPO_4.7H_2O$ | 41.23 | |
| | | 2.2341 g/100 mL (total weight) | | |
| D | 7.50 | 2 g/100 mL of BSA | | |
| | | 0.1210191 g/100 mL of $NaH_2PO_4$ | 8.769 | 49.999 |
| | | 1.11309 g/100 mL of $Na_2HPO_4.7H_2O$ | 41.23 | |
| | | 3.2341 g/100 mL (total weight) | | |
| E | 5.00 | 0.52508 g/100 mL of citric acid | 25 | — |
| | | 1.34848 g/100 mL of $Na_2HPO_4.7H_2O$ | 50 | |
| | | 40 mg/100 mL of o-phenylenediamine hydrochloride | | |
| | | 1.913567 g/100 mL (total weight) | | |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of determining the acetylation phenotype of an individual, which comprises:

a) measuring the molar ratio of first and second different metabolites of caffeine in a biological sample of an individual after drinking coffee with at least two antibodies each specific to a different metabolite of caffeine wherein said antibodies do not cross-react with 1,7-dimethylxanthine (DMX) and, wherein a molar ratio below about 1.80 is indicative of low acetylation phenotype of said individual.

2. The method of claim 1, wherein the first caffeine metabolite is selected from the group consisting of 5-acetyl-6-amino-1-methyluracil (AAMU), 5-acetyl-6-formylamino-1-methyluracil (AFMU), and those illustrated in FIGS. 2 and 3; and the second caffeine metabolite is selected from the group consisting of 1-methyl xanthine (1X), and those illustrated in FIGS. 4 and 5.

3. The method of claim 2, wherein said biological sample is a urine sample.

4. The method of claim 3, wherein the determined acetylation phenotype of said individual allows physicians to predict susceptibility to carcinogen induced diseases.

5. A competitive antigen enzyme linked immunosorbent assay (ELISA) method for determining N-acetyltransferase (NAT2) phenotype, which comprises:

a) measuring the molar ratio of first and second different metabolites of caffeine in a biological sample of an individual after drinking coffee with two antibodies each specific to a different metabolite of caffeine wherein said antibodies do not cross-react with 1,7-dimethylxanthine(DMX) and, wherein a molar ratio below about 1.80 is indicative of low acetylation phenotype of said individual.

6. The ELISA method of claim 5, wherein the first caffeine metabolite is selected from the group consisting of 5-acetyl-6-amino-1-methyluracil (AAMU), 5-acetyl-6-formylamino-1-methyluracil (AFMU), and those illustrated in FIGS. 2 and 3; and the second caffeine metabolite is selected from the group consisting of 1-methyl xanthine (1X), and those illustrated in FIGS. 4 and 5.

7. The ELISA method of claim 5, wherein said biological sample is a urine sample.

8. The ELISA method of claim 5, wherein the determined acetylation phenotype of said individual allows a physician to predict susceptibility to carcinogen induced diseases.

9. A competitive enzyme linked immunosorbent assay (ELISA) kit for determining N-acetyltransferase (NAT2) phenotype, which comprises at least two antibodies each specific to a different metabolite of caffeine to measure their molar ratio in biological sample of an individual after drinking coffee wherein said antibodies do not cross-react with 1,7-dimethylxanthine(DMX) and, wherein said molar ratio is indicative of the acetylation phenotype of said individual.

10. The competitive ELISA kit of claim 9, further comprises:

a) a plate coated with a first antibody specific to a first metabolite of caffeine;

b) a second antibody specific to a second metabolite of caffeine;

c) a known amount of AAMU-horseradish peroxidase conjugate; and d) a known amount of 1X-horseradish peroxidase conjugate.

11. The method of claim 1 wherein said specific antibodies are polyclonal or monoclonal antibodies.

12. The method of claim 1 wherein said antibodies are polyclonal.

13. The competitive antigen enzyme linked immunosorbent assay (ELISA) of claim 5 wherein said specific antibodies are polyclonal or monoclonal antibodies.

14. The competitive antigen enzyme linked immunosorbent assay of claim 5 wherein said antibodies are polyclonal.

15. The competitive ELISA kit of claim 10 wherein said specific antibodies are polyclonal or monoclonal antibodies.

16. The competitive ELISA kit of claim 10 wherein said specific antibodies are polyclonal antibodies.

* * * * *